(12) United States Patent
Bissot

(10) Patent No.: US 10,232,659 B2
(45) Date of Patent: Mar. 19, 2019

(54) COMBINATION FLOWER PRESS AND NOTEBOOK

(71) Applicant: Daniel Christopher Bissot, Woodsboro, MD (US)

(72) Inventor: Daniel Christopher Bissot, Woodsboro, MD (US)

( * ) Notice: Subject to any disclaimer, the term of this patent is extended or adjusted under 35 U.S.C. 154(b) by 85 days.

(21) Appl. No.: 15/240,739

(22) Filed: Aug. 18, 2016

(65) Prior Publication Data

US 2018/0050552 A1 Feb. 22, 2018

(51) Int. Cl.
*B42D 3/12* (2006.01)
*B42D 3/10* (2006.01)
*B42D 1/00* (2006.01)
*A01N 3/00* (2006.01)
*B42D 3/02* (2006.01)

(52) U.S. Cl.
CPC ............ *B42D 3/12* (2013.01); *A01N 3/00* (2013.01); *B42D 1/006* (2013.01); *B42D 1/007* (2013.01); *B42D 3/02* (2013.01); *B42D 3/10* (2013.01)

(58) Field of Classification Search
None
See application file for complete search history.

(56) References Cited

U.S. PATENT DOCUMENTS

| | | | | |
|---|---|---|---|---|
| 3,191,319 A | * | 6/1965 | Waisgerber | B42F 5/00 206/232 |
| 3,852,891 A | * | 12/1974 | Stephan | A01N 3/00 34/71 |
| 5,230,767 A | * | 7/1993 | Taylor | A01N 3/00 100/297 |
| 5,693,384 A | * | 12/1997 | Hollinger, Jr. | B32B 27/10 428/34.2 |
| 5,948,311 A | * | 9/1999 | Beecroft | F26B 3/347 156/580 |
| 6,068,115 A | * | 5/2000 | Boulton | B65D 5/4204 206/232 |

FOREIGN PATENT DOCUMENTS

JP 09078324 A * 3/1997

* cited by examiner

*Primary Examiner* — Sarah B McPartlin

(57) ABSTRACT

A device consisting of the combination of an outdoor field notebook and flower press having a plurality of pages for writing and a plurality of stock inserts disposed between opposing, bounded covers. The pages are adapted for writing, sketching, and general note-taking. The stock inserts provide a base for pressing organic material specimens there between. The opposing, bound covers include aligning press holes though which mating fasteners are threaded and tightened. The covers serve as the platens between which organic specimens are placed and dried for preservation.

1 Claim, 5 Drawing Sheets

COMBINATION FLOWER PRESS AND NOTEBOOK

BACKGROUND OF THE INVENTION

The present invention relates to flower presses and notebooks and, more particularly, a bounded combination flower press and outdoor field notebook facilitating the combined use of a traditional field journal and pressing of organic material specimens.

Outdoor activities often require that field notes be written and organic material specimens be collected for further study, these are traditionally accomplished by use of two or more devices, which can be cumbersome and add unnecessary weight to carry. Especially since traditional flower presses are not designed to be portable.

As can be seen, there is a need for a bounded combination flower press and outdoor field notebook enabling users to take field notes as well as press organic specimens all in the same device, reducing the number of devices and correspondingly weight carried.

DETAILED DESCRIPTION OF THE INVENTION

Figure 1:
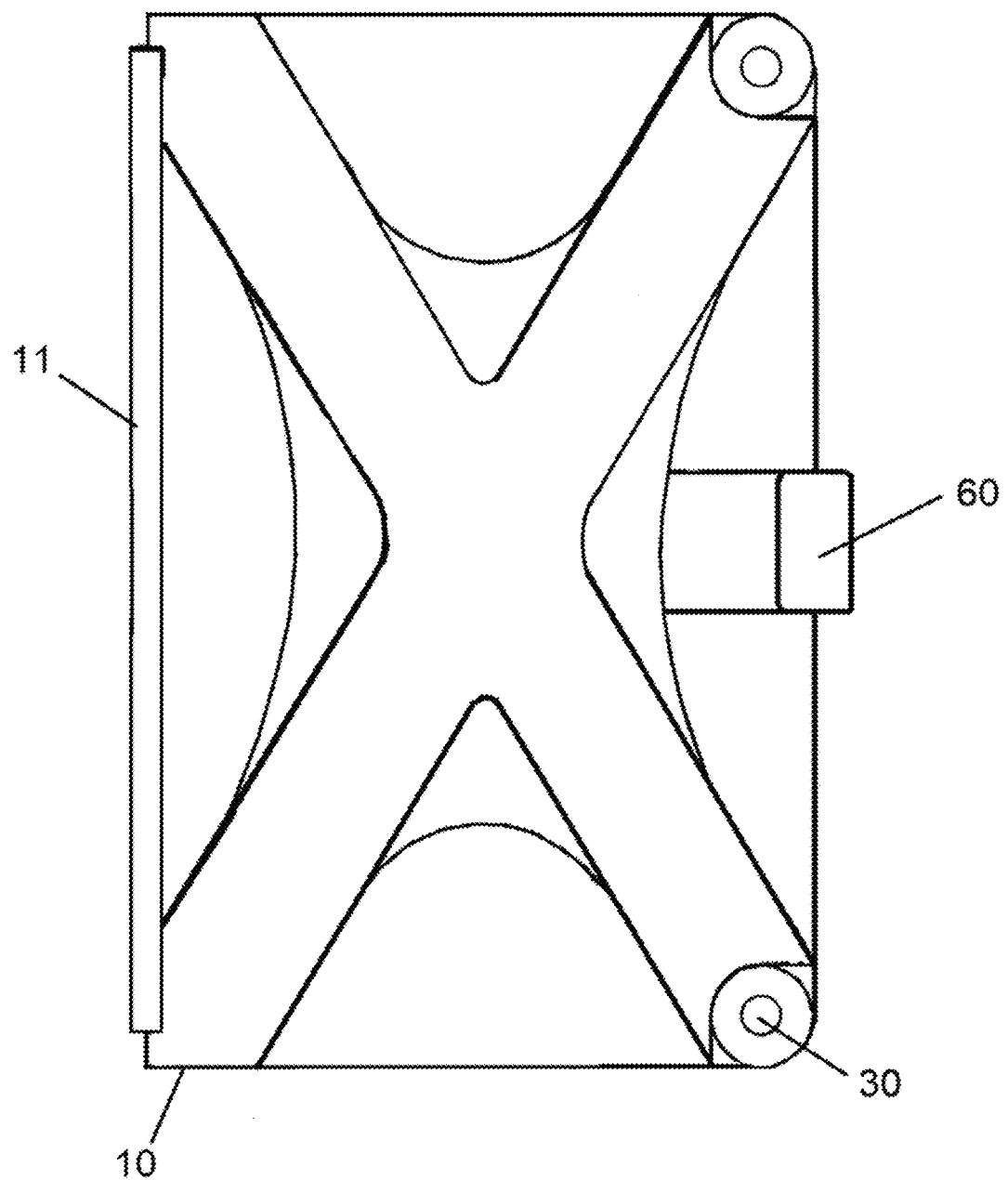
FIG. 1 is a top view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the present invention.

Broadly, an embodiment of the present invention provides a combination flower press and notebook having plurality of layers of paper and a plurality of layers of stock inserts disposed between each two layers of paper, wherein the papers and stock inserts are disposed between opposing, bounded front and back covers, movable between a closed and open configuration. The papers are adapted for writing, drawing and other forms of note-taking, while the insert stocks provide a base or platform for pressing organic material there between. The opposing covers provide press holes for selectively operating mating fasteners for exerting the required pressure on and between the opposing covers when pressing the organic material. The present invention provides a latch mechanism for removably securing the opposing covers when the mating fasteners are not installed.

Referring now to FIGS. 1 through 5, the present invention may include a combination flower press and notebook ("press notebook") 100. The press notebook 100 may include a plurality of layers of paper 20 and stock inserts 50 disposed between opposing front and back covers 10. The covers 10 may be made from a variety of inorganic materials suitable for providing structural integrity and protection of the papers 20 as well as serving as platens between which organic material 70 is pressed. In certain embodiments, the covers 10 may be made of rigid plastic or various plasticized material. In certain embodiments, each cover 10 may have ideal dimensions of 5×7.5 inches.

Figure 3:
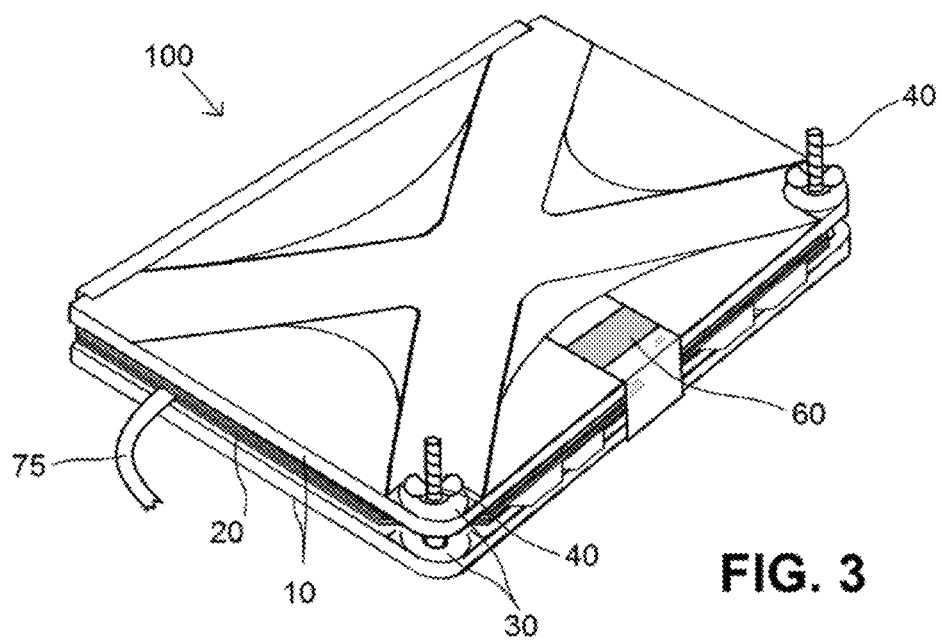
FIG. 3 is a perspective view of an exemplary embodiment of the present invention, shown in a closed configuration.
Figure 4:
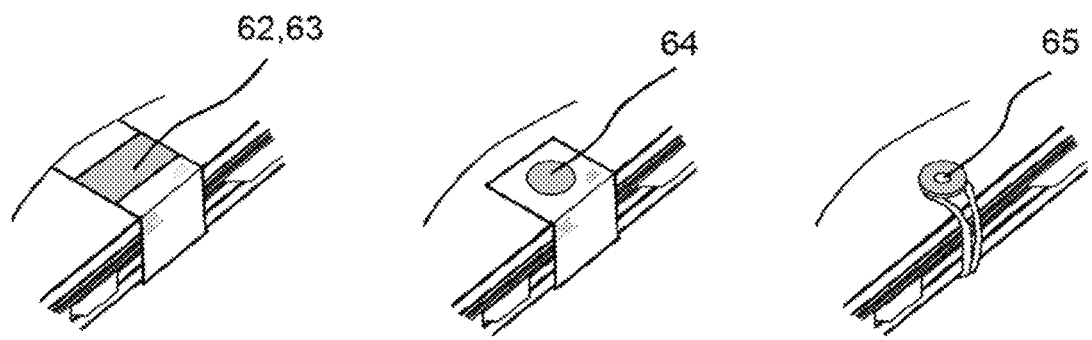
FIG. 4 show various detailed perspective views of an exemplary embodiment of the latch mechanism of the present invention.
Figure 5:
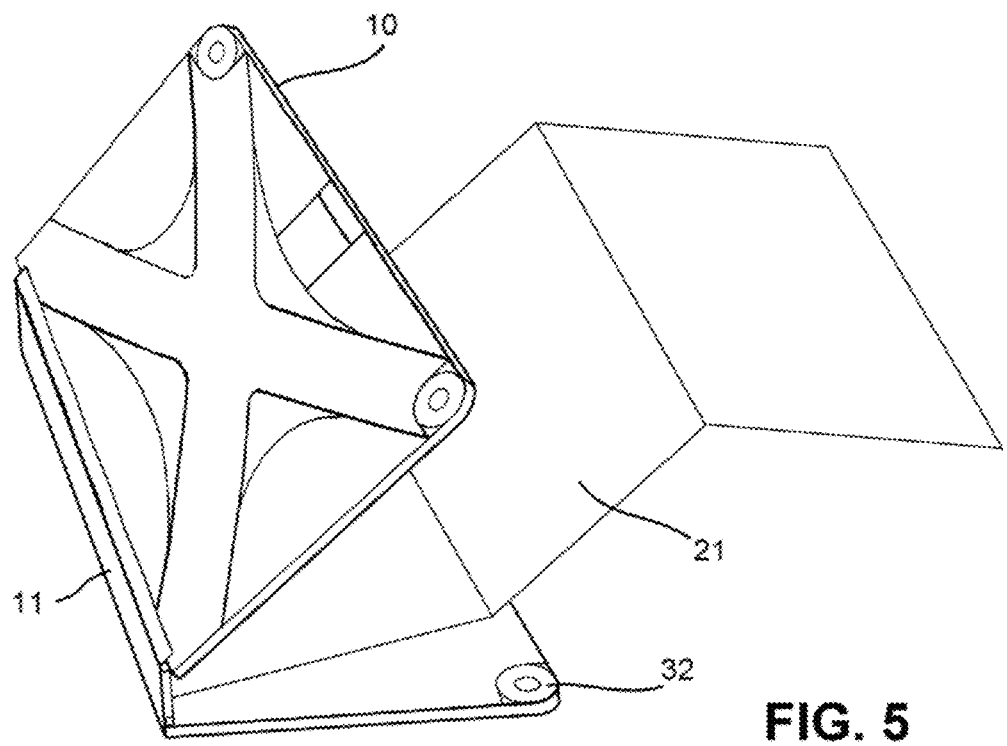
FIG. 5 is a perspective view of an exemplary embodiment of the present invention, illustrating a folded pages embodiment shown in an open configuration.

The covers 10 are attached together along one edge by a binder 11, such as a double hinged spine or the like, so that the opposing covers 10 are movable between a closed configuration and an open configuration, as illustrated in FIGS. 3 and 5, respectively. The binder 11 can be constructed of the same material as the covers 10, however due to its frequent use and likelihood of physical wear and impact from the intended outdoor use of the present invention, a strong-wear resistant metal would be preferred. Each cover 10 may provide press holes 30 that go through the covers 10 and align with the press holes 30 provided by the opposite cover 10 when in the closed configuration. Each press hole 30 may be disposed near and inward from each corner of each cover 10. In certain embodiments, the press holes 30 may be circumscribed by a reinforcing metal disk 32 such as a washer that serves to prevent wear of the cover 10 surrounding the press holes 30.

While the press notebook 100 is in the closed configuration, the press holes 30 align, facilitating installation of the plurality of mating fastener combination sets ("mating fasteners") 40, wherein the mating fasteners 40 may be threaded through the aligned press holes 30 and then tightened (as seen in FIG. 3). The mating fasteners 40 may be a bolt and complementary wing-nut or the like. The installation of the mating fasteners 40 are adapted for exerting pressure required for the pressing and drying of the organic material specimens 70.

While the mating fasteners 40 sets are not installed a latch mechanism 60 insures that the covers remain closed when not in use. The latch mechanism 60 may include flexible nylon and be detachably connected by way of a hook 62 and loop 63 VELCRO system. However the latch mechanism 60 may also be secured by way of magnets 64 or by a button and elastic string system 65. If hook and loop VELCRO or magnetic systems were to be used for the latch then flexible loops 61 could be sewn into the flap as a place where pencils, pens, or other writing utensils could be stored.

Inserted between the covers 10, the plurality of layers of paper 20 may be adapted so that a user may transcribe, draw, sketch, write, etc., thereon. These layers of paper 20 could be made from a range of materials including traditional acid-free pulp based paper, hydrophobic coated pulp paper, or preferably stone or carbonate based paper which has the ideal physical characteristics for the intended outdoor use of the invention. These layers of paper 20 may be arranged and inserted in a multitude of styles that suit the need of the invention, for example several pages could be of larger dimensions and folded 21, as exemplified in FIG. 5.

Figure 2:
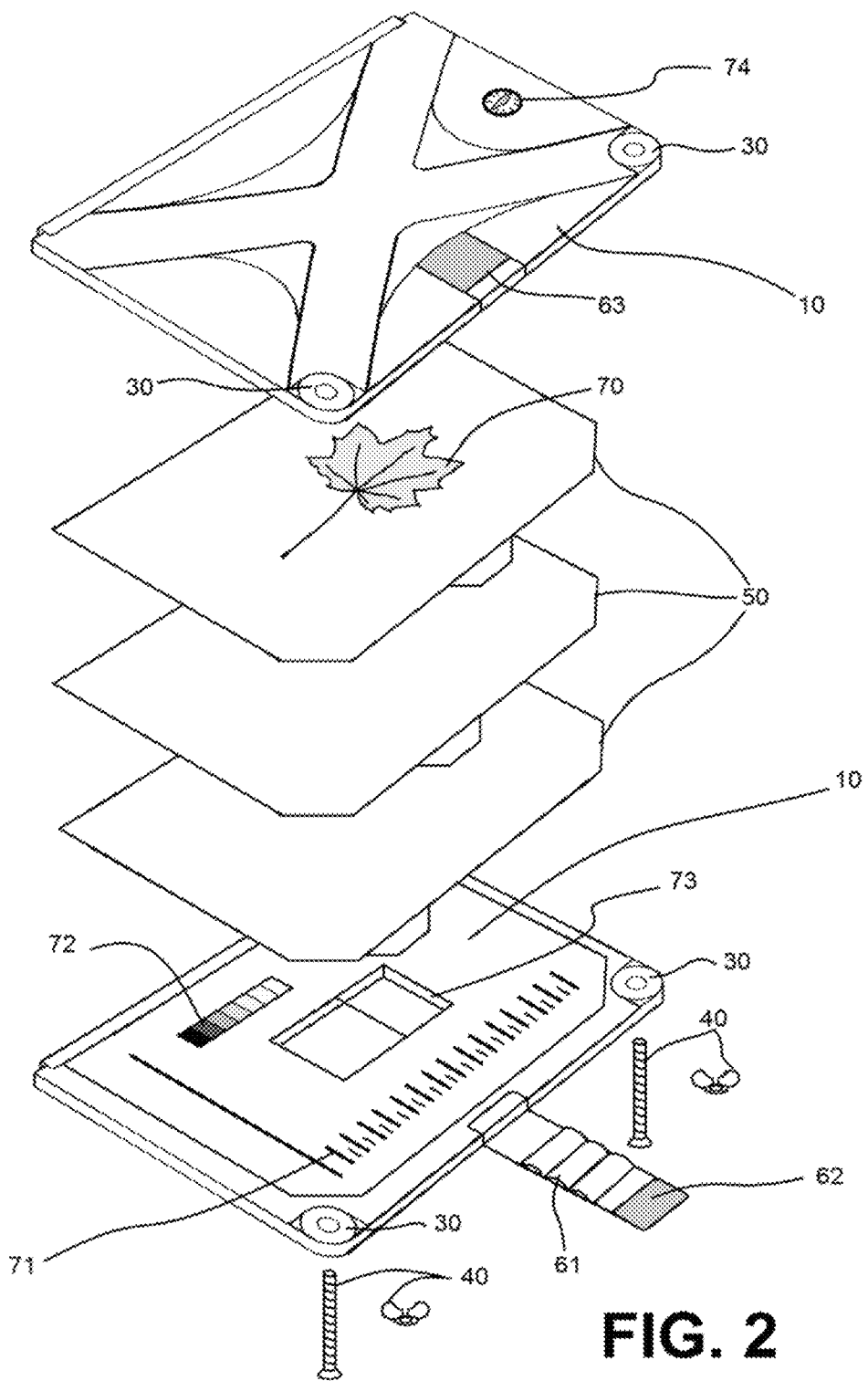
FIG. 2 is an exploded view of an exemplary embodiment of the present invention.

In addition, a plurality of thicker card stock inserts 50 are disposed within the layers of paper 20. The stock inserts 50 may be adapted to provide a platform on which the organic material specimens 70 would be pressed and preserved, and to separate them from the writing pages/paper 20. These inserts 50 could be easily located within the press notebook 100 by use of tabs located on the side of the inserts 50, as illustrated in FIG. 2.

Additional features that could be added to the press notebook 100 to enhance the functionality of the press notebook 100 include, but are not limited to, button compass 74—placed on the exterior of the cover 10 a button compass would assist in the navigation and orientation of the user in the field; liquid crystal thermometer 72—adhered to the inside of the front or back cover 10 a low-profile liquid crystal thermometer would serve as a rough temperature gauge so that the user may record current weather conditions; photograph scale 71—incorporated onto the inside of the front or back cover 10 a scale would provide a measuring ruler as well as a photograph scale when placed next to the object being photographed; cover pocket 73—engraved into the inside of the front and/or back covers 10 thin pockets could be designed to allow for the placement of attachments such as folded guides, credit-cards, or credit-card sized objects such as a folding wallet knife; and/or ribbon bookmark 75—a basic fabric ribbon bookmark for marking pages attached to cover at one end.

It should be understood, of course, that the foregoing relates to exemplary embodiments of the invention and that modifications may be made without departing from the spirit and scope of the present invention.

What is claimed is:

1. A combination flower press and outdoor field notebook comprising:
   a plurality of layers of paper and a plurality of stock inserts, wherein one of said plurality of stock inserts is disposed between each of the layers of paper;
   opposing rigid front and rigid back covers attached together along one edge by a binder such that the opposing rigid front and rigid back covers are movable between closed and open configurations;
   a plurality of press holes extending through said rigid front cover and aligned with a corresponding plurality of press holes extending through said rigid back cover to form a plurality of press hole pairs; and
   a mating fastener set threaded through each of the plurality of press hole pairs, wherein each mating fastener set can be tightened to aid in drying and preservation of organic material placed between the plurality of stock inserts.

* * * * *